(12) United States Patent
Borom (10) Patent No.: US 7,108,422 B2
(45) Date of Patent: Sep. 19, 2006

(54) INTEGRATED SURGICAL TABLE DRAPE

(76) Inventor: Andrew H. Borom, 3656 Uncle Glover Rd., Tallahassee, FL (US) 32312

( * ) Notice: Subject to any disclaimer, the term of this patent is extended or adjusted under 35 U.S.C. 154(b) by 590 days.

(21) Appl. No.: 10/647,563

(22) Filed: Aug. 25, 2003

(65) Prior Publication Data

US 2005/0047734 A1    Mar. 3, 2005

(51) Int. Cl.
*H05G 1/00* (2006.01)
(52) U.S. Cl. .................... 378/204; 378/193
(58) Field of Classification Search ............. 378/193, 378/195–198, 203–204; 128/849–856
See application file for complete search history.

(56) References Cited

U.S. PATENT DOCUMENTS

| | | | |
|---|---|---|---|
| 3,715,587 A | 2/1973 | Burkhalter et al. | |
| 5,001,739 A | 3/1991 | Fischer | |
| 5,490,524 A | 2/1996 | Williams et al. | |
| 5,515,415 A | 5/1996 | Herrmann et al. | |
| 5,802,719 A | 9/1998 | O'Farrell, Jr. et al. | |
| 5,822,814 A | 10/1998 | Van der Ende | |
| 6,113,265 A | 9/2000 | Babler | |
| 6,256,374 B1 | 7/2001 | Tomasetti et al. | |
| 6,285,902 B1 * | 9/2001 | Kienzle, III et al. | 600/427 |
| 6,322,251 B1 | 11/2001 | Ballhaus et al. | |
| 6,448,571 B1 | 9/2002 | Goldstein | |

* cited by examiner

*Primary Examiner*—Edward J. Glick
*Assistant Examiner*—Hoon Song
(74) *Attorney, Agent, or Firm*—John Wiley Horton (57) ABSTRACT

A sterilizing drape which can be used to cover a C-arm machine in combination with a small surgical table. The invention assumes that a small surgical table has been affixed to the lower portion of a C-arm machine. The sterilizing drape covers the exposed portions of the C-arm machine as well as the small surgical table. An integrated version is disclosed which covers the C-arm machine, the small surgical table, and the patient. Other embodiments are disclosed which cover these areas using separate pieces.

23 Claims, 15 Drawing Sheets

INTEGRATED SURGICAL TABLE DRAPE

BACKGROUND OF THE INVENTION

1. Field of the Invention

This invention relates to the field of medicine. More specifically, the invention comprises a surgical drape which is configured to cover a common type of X-ray machine in combination with a small surgical table.

2. Description of the Related Art

Figure 1:
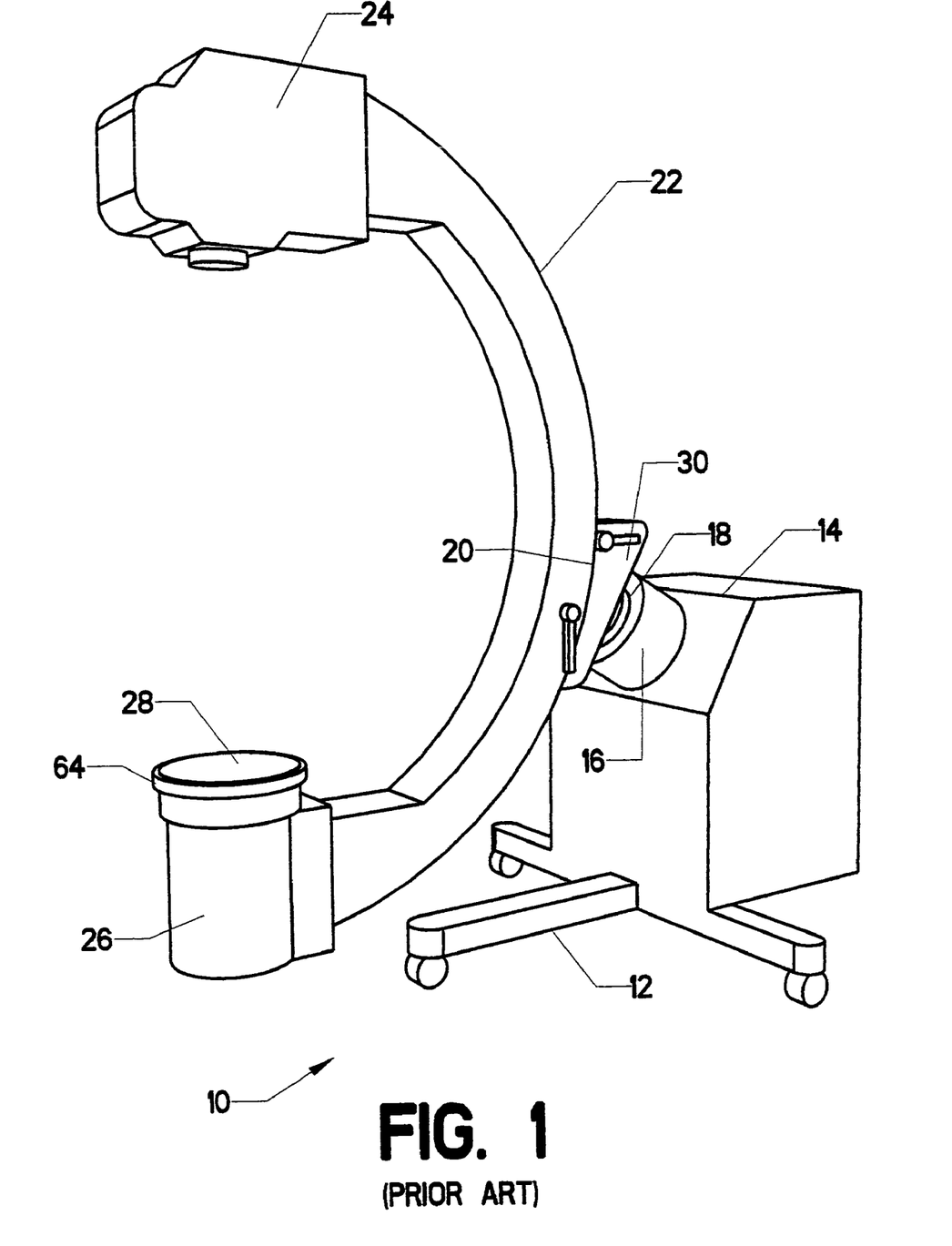
FIG. 1 is a perspective view, showing a prior art C-arm X-ray machine.

X-ray machines have been used in the practice of medicine for many decades. One such machine in common use is referred to as a "C-arm" machine. FIG. 1 depicts one example of such a machine. Those skilled in the art will know that a wide variety of such machines are in use. They generally share the same major components, however.

C-arm machine 10 is supported by base 12, which is typically furnished with lockable castors so that the machine can be easily moved to a desired location and fixed. Main housing 14 attaches to the base. This element provides structural support and also often houses the necessary electronic equipment. Sliding joint support 16 protrudes upward and forward from main housing 14. Pivot joint 18 rotatably attaches C-arm support 30 to sliding joint support 16. C-arm 22 is slidably attached to sliding joint support 16 by sliding joint 20. In the particular type of machine illustrated, pivot joint 18 and sliding joint 20 can be adjusted as desired—then locked into position.

The reader should be aware that not all C-arm machines have the adjustment features described. Simpler machines may be fixed in the position shown. The invention described hereinafter typically employs the C-arm machine in the position shown. Thus, the various adjustment features which a particular machine may possess are not significant to the present invention.

C-arm machine 10, like most X-ray devices, includes an emitter 24 and image intensifier 26. Though a discussion of X-ray machine technology is beyond the scope of this disclosure, those skilled in the art will know that emitter 24 generates X-rays and image intensifier 26 is generally configured to receive these rays and provide a useable image. Those skilled in the art will also know that the position of emitter 24 and image intensifier 26 may be reversed.

BRIEF SUMMARY OF THE INVENTION

The present invention comprises a sterilizing drape which can be used to cover a C-arm machine in combination with a small surgical table. The invention assumes that a small surgical table has been affixed to the lower portion of a C-arm machine. The sterilizing drape covers the exposed portions of the C-arm machine as well as the small surgical table. An integrated version is disclosed which covers the C-arm machine, the small surgical table, and the patient. Other embodiments are disclosed which cover these areas using separate pieces.

REFERENCE NUMERALS IN THE DRAWINGS

| | | | |
|---|---|---|---|
| 10 | C-arm machine | 12 | base |
| 14 | main housing | 16 | sliding joint support |
| 18 | pivot joint | 20 | sliding joint |
| 22 | C-arm | 24 | emitter |
| 26 | image intensifier | 28 | mounting surface |
| 30 | C-arm support | 32 | surgical table |
| 52 | cylindrical surface | 54 | conventional table |
| 56 | head support | 64 | integrated drape |
| 66 | conventional drape | 68 | C-arm portion |
| 70 | table portion | 72 | patient portion |
| 74 | patient | 76 | arm |
| 78 | cuff | 80 | open seam |
| 82 | closure | 84 | emitter enclosure |
| 86 | relief cut | 88 | hanging portion |
| 90 | elastic ring | 92 | emitter window |
| 94 | C-arm drape | 96 | table drape |
| 98 | relief cut | 100 | lower C-arm cover |
| 102 | side panel | 104 | end panel |
| 106 | seam | 108 | upper panel |
| 110 | integral table drape | 112 | fold back |
| 114 | elastic strap | 116 | split flap |
| 118 | solid flap | 120 | elastic panel cuff |
| 122 | cuff hole | | |

DETAILED DESCRIPTION OF THE INVENTION

FIG. 1 shows prior art C-arm machine 10. It is generally used to X-ray specific regions of a patient's anatomy. Base 12 is provided with castors which allow the machine to be rolled into a desired location. Pivot joint 18 can be rotated to angularly displace the plane in which C-arm 22 resides. Sliding joint 20 can be unlocked to allow C-arm 22 to slide along the arc of its curvature. Thus, C-arm 22 is ultimately adjustable in roll and pitch.

C-arm 22 structurally mounts emitter 24 and image intensifier 26. Emitter 24 controllably emits a stream of X-rays toward image intensifier 26. Image intensifier 26 receives the stream of X-rays and enhances them for visualization, which is typically accomplished through a computer monitor. The anatomical features to be X-rayed must generally be placed proximate a line drawn between emitter 24 and image intensifier 26.

Many types of C-arm machines are in common use. The relative location of the emitter and image intensifier may be reversed on some machines. The mounting and positioning features of other machines are also different from the one shown in FIG. 1. The present invention is suitable for use with a wide variety of machines, and should not be viewed as limited to any one particular type.

Figure 2:
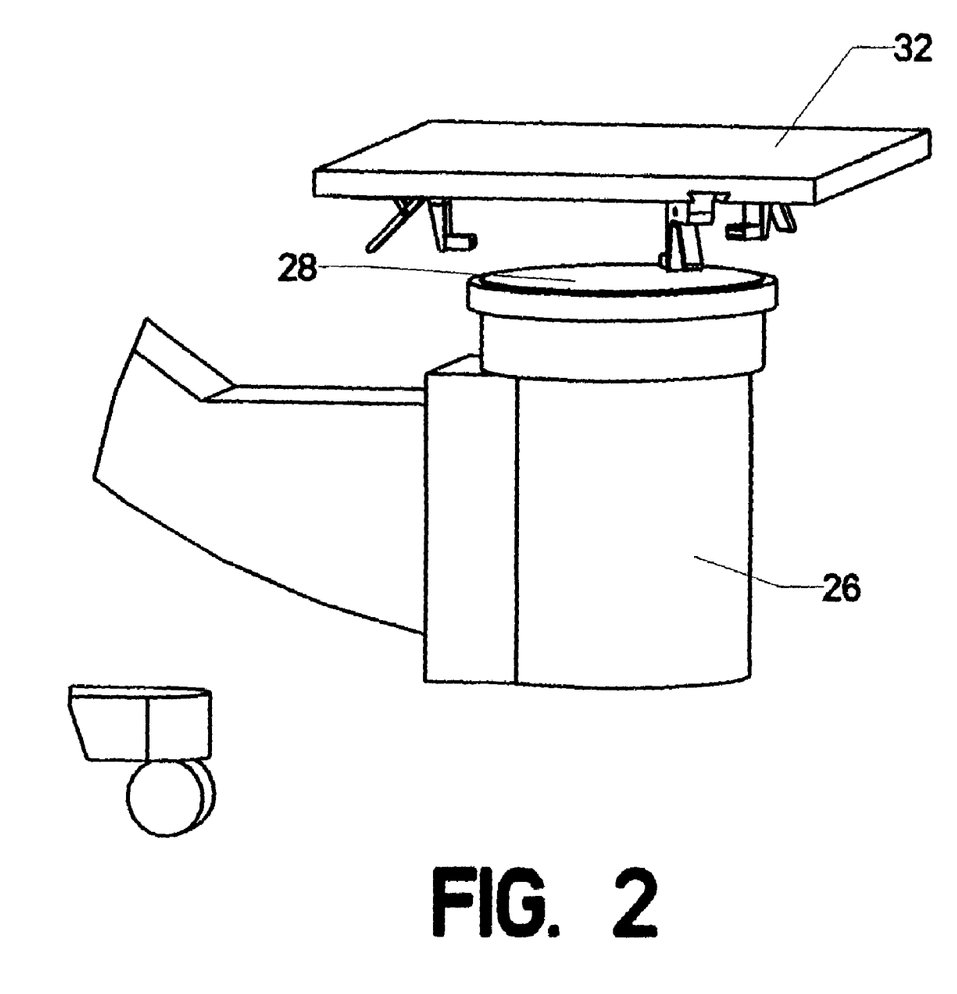
FIG. 2 is a perspective view, showing the attachment of a small surgical table to the C-arm machine.
Figure 3:
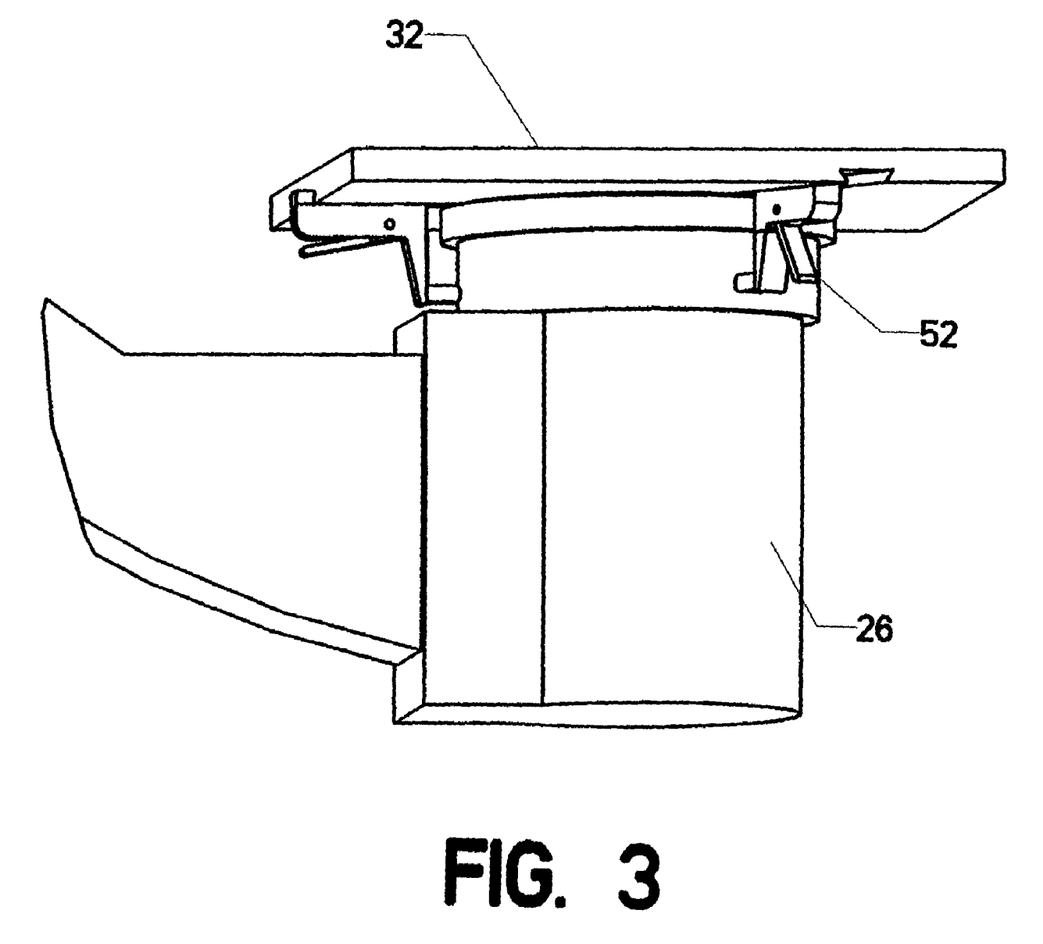
FIG. 3 is a perspective view, showing the attachment of a small surgical table to the C-arm machine.

The present invention contemplates the attachment of a small surgical table to a lower portion of a C-arm machine. Details of such a small surgical table are disclosed in my copending application entitled "ATTACHABLE SURGICAL TABLE," which is hereby incorporated by reference. FIG. 2 shows surgical table 32 in position over mounting surface 28 of image intensifier 26. FIG. 3 shows surgical table 32 actually attached to cylindrical surface 52 of image intensifier 26. The particular table shown is attached via clamping means. The reader should appreciate that the type of small surgical table and the method used to attach it are of no particular importance to the present surgical drape invention, which can be adapted for use with a wide variety of such tables.

A small surgical table affixed directly to the C-arm machine allows a surgeon to perform surgical procedures directly over the X-ray image intensifier. Accurate X-ray visualization of the anatomy proximate the surgical site is therefore enhanced.

Figure 4:
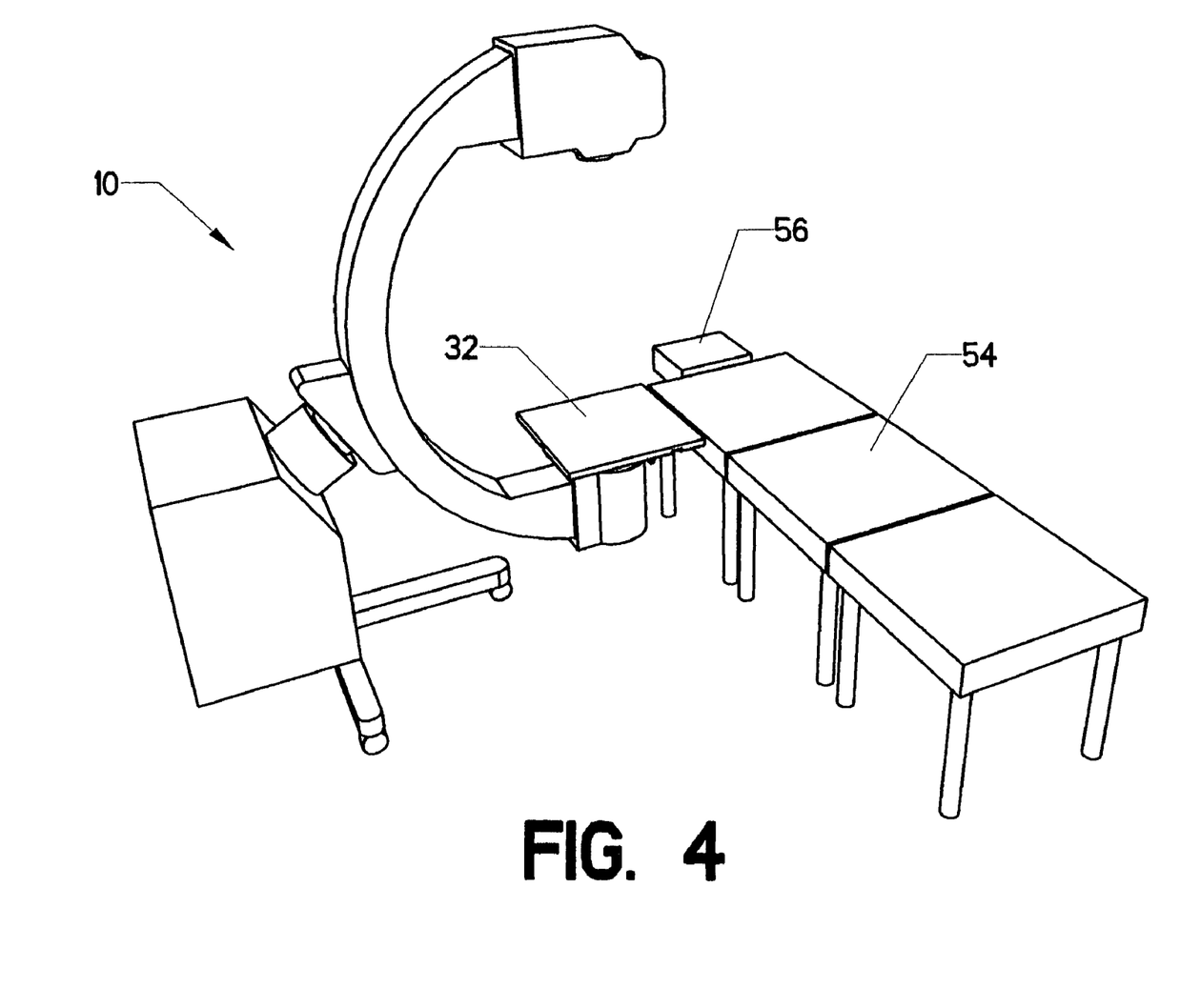
FIG. 4 is a perspective view, showing the small surgical table positioned adjacent to a conventional surgical table.

Surgical table 32 is preferably used in conjunction with prior art devices for holding the patient in position. FIG. 4 shows one possible configuration. C-arm machine 10 with attached surgical table 32 is placed next to conventional table 54 with head support 56. The patient is placed face-up on conventional table 54. The patient's right arm would then be extended out to the patient's right, where the patient's hand/wrist area could be secured to surgical table 32. The surgeon would then perform a procedure on the patient's hand while it remains affixed to surgical table 32.

As one example—the surgeon may need to place orthopaedic hardware in the patient's hand to repair a fracture. X-ray images can be taken before, during, and after the placement of the hardware to ensure the surgeon's satisfaction with the placement.

Those skilled in the art will know that a surgical environment is preferably sterile. Thus, most equipment used in this environment is either small enough to be placed in a sterilizing machine, or covered with a sterile drape. Obviously, the C-arm machine and surgical table are too large to be placed within conventional sterilization machines (not to mention the obvious concerns regarding elevated temperatures). Thus, they must be covered with a sterile drape.

Figure 5:
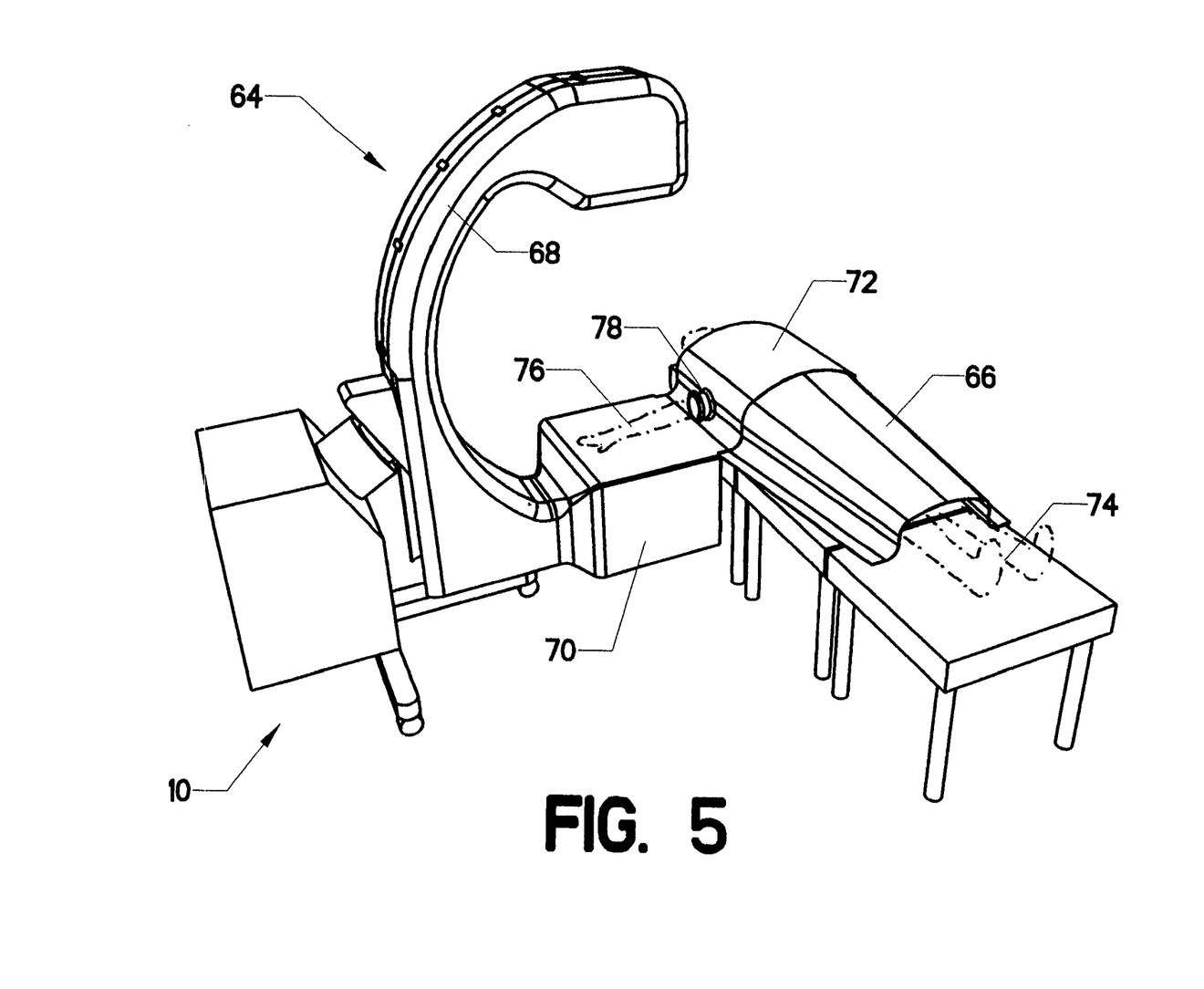
FIG. 5 is a perspective view, showing the present invention covering a C-arm machine, the small surgical table, and a portion of the patient.

FIG. 5 shows the configuration of FIG. 4 with the addition of integrated drape 64. Patient 74 is depicted in one common position using the dashed lines. Integrated drape 64 covers the portions of C-arm machine 10 which are proximate the surgical site, surgical table 32, and a portion of patient 74. It is broadly divided into three regions—C-arm portion 68, table portion 70, and patient portion 72. Patient portion 72 is preferably provided with a cuff 78, through which the patient's arm 76 is inserted and exposed. The balance of patient 74 is typically covered with one or more conventional drapes 66.

Figure 6:
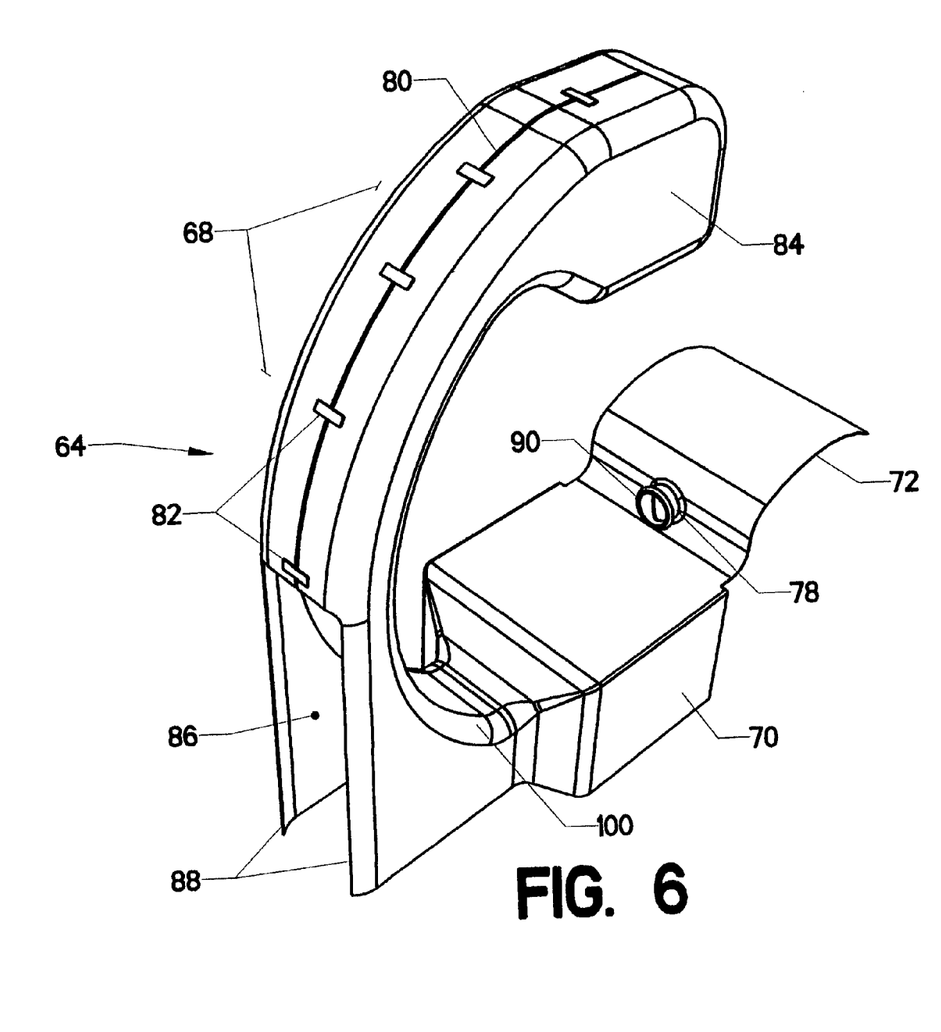
FIG. 6 is a perspective view, showing the present invention alone.

FIG. 6 shows integrated drape 64 standing alone. C-arm portion 68 is bisected by open seam 80, which allows the fabric to be pulled apart in order to slip over a C-arm machine and into the appropriate position. Open seam 80 is fastened together by a plurality of closures 82. These can be buttons, snaps, hooks, or many other types of conventional closures. In the embodiment shown, they are VELCRO strips. The upper extreme of C-arm portion 68 is emitter enclosure 84. With respect to FIGS. 1 and 6, those skilled in the art will realize that integrated drape 64 can be installed by opening open seam 80, then slipping emitter enclosure 84 around emitter 24. The user then pulls open seam 80 closed over the upper portion of C-arm 22, securing it with closures 82. Relief cut 86 is provided to accommodate C-arm support 30, pivot joint 18, and sliding joint support 16, as well as to provide access to the adjustment features of the C-arm machine. Hanging portions 88 form the sides of relief cut 86. These portions cover the aforementioned joints and adjustment features. Finally, the bottom of C-arm portion 68 is formed into lower C-arm cover 100, which covers the top and sides of the lower portion of C-arm 22.

Referring now to FIGS. 4 and 6, the reader will observe that table portion 70 lies over the top and three sides of surgical table 32. It is joined to lower C-arm cover 100, preferably using a generously expanding transition, so that the integrated drape can accommodate a variety of C-arm machines and surgical tables.

The open side of table portion 70 is joined to patient portion 72. Patient portion 72 preferably opens into a cuff 78, which resembles a short sleeve on a shirt. Cuff 78 is bounded by elastic ring 90. In operation, the patient's arm is thrust through cuff 78 and advanced until the surgical site lies over surgical table 32. Elastic ring 90 seals cuff 78 against the patient's arm in order to form a sterile environment in the proximity of surgical table 32.

Figure 7:
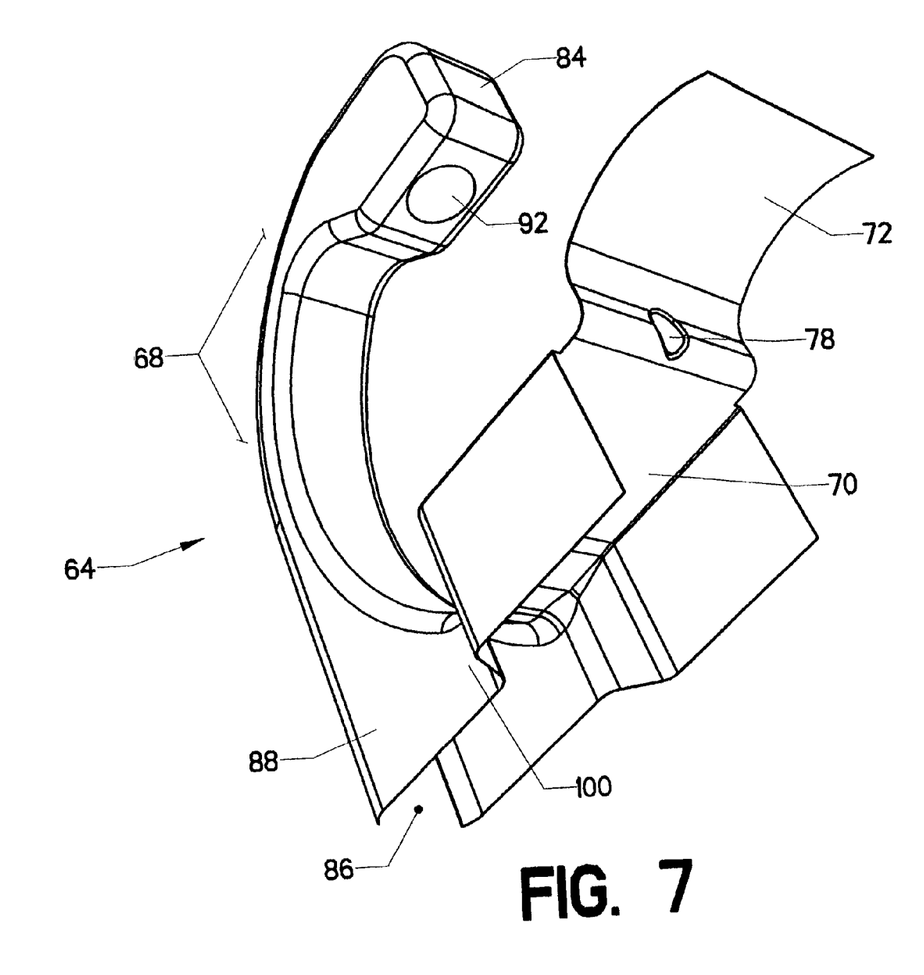
FIG. 7 is a perspective view, showing the present invention alone.

FIG. 7 shows integrated drape 64 from a different perspective. The reader will observe that the lower portions of lower C-arm cover 100 and table portion 70 are open, in order to facilitate installation. The reader will also observe the presence of emitter window 92 on th-e bottom of emitter cover 84. Integrated drape 64 is preferably made of X-ray transparent material. In some instances, however, it may be cheaper to use X-ray transparent material in only selected areas. As an example, an X-ray transparent material can be used only in the region of emitter window 92. It may also be desirable in some instances to use X-ray transparent material for the upper surface of table portion 70.

Figure 8:
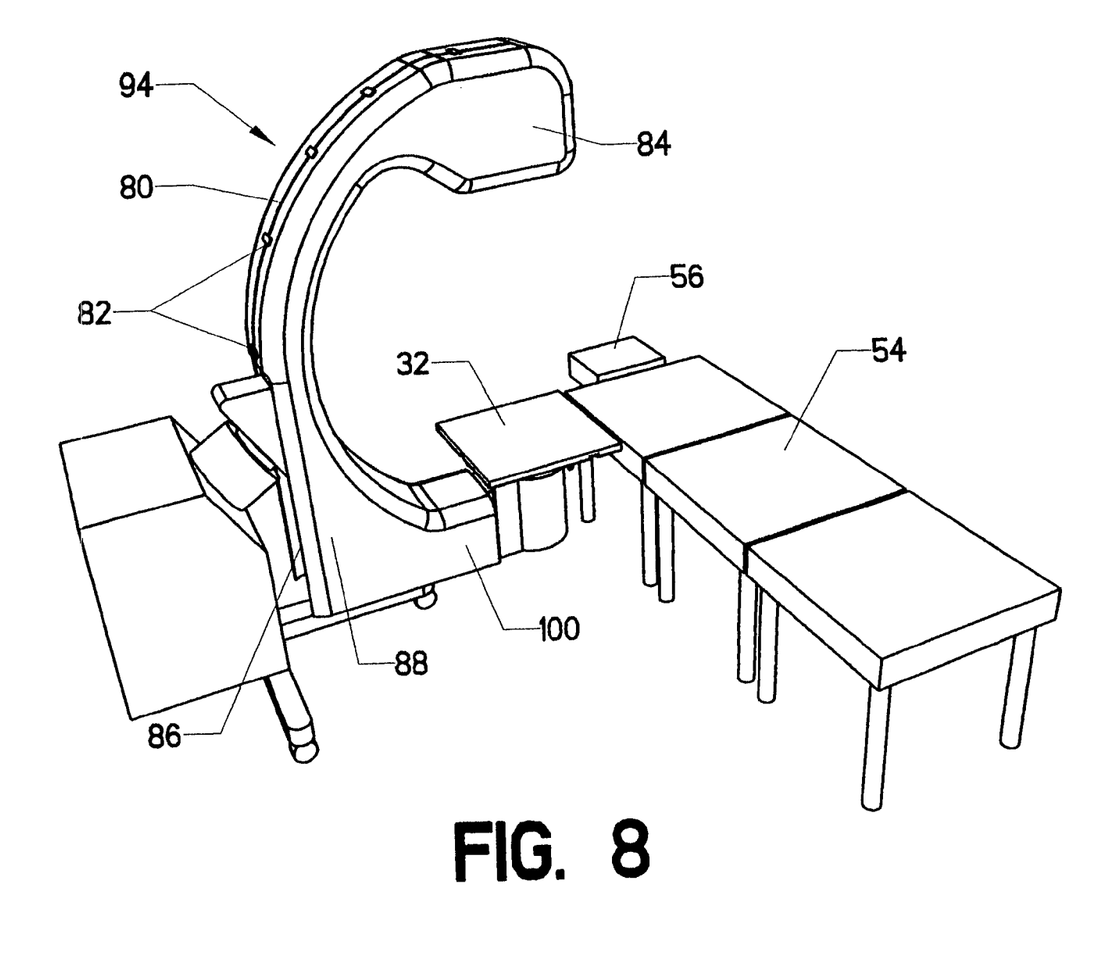
FIG. 8 is a perspective view, showing an alternate embodiment of the present invention.

Those skilled in the art will realize that integrated drape 64 can be divided into smaller separate portions. This division might make it easier to manufacture, as well as possibly easier to install. FIG. 8 shows the same configuration shown previously in FIG. 4. However, in FIG. 8, an alternate embodiment of the drape is disclosed. C-arm drape 94 covers only the items covered by C-arm portion 68 of integrated drape 64. All its other features (open seam 80, closures 82, etc.) are identical to the features of C-arm portion 68.

Figure 9:
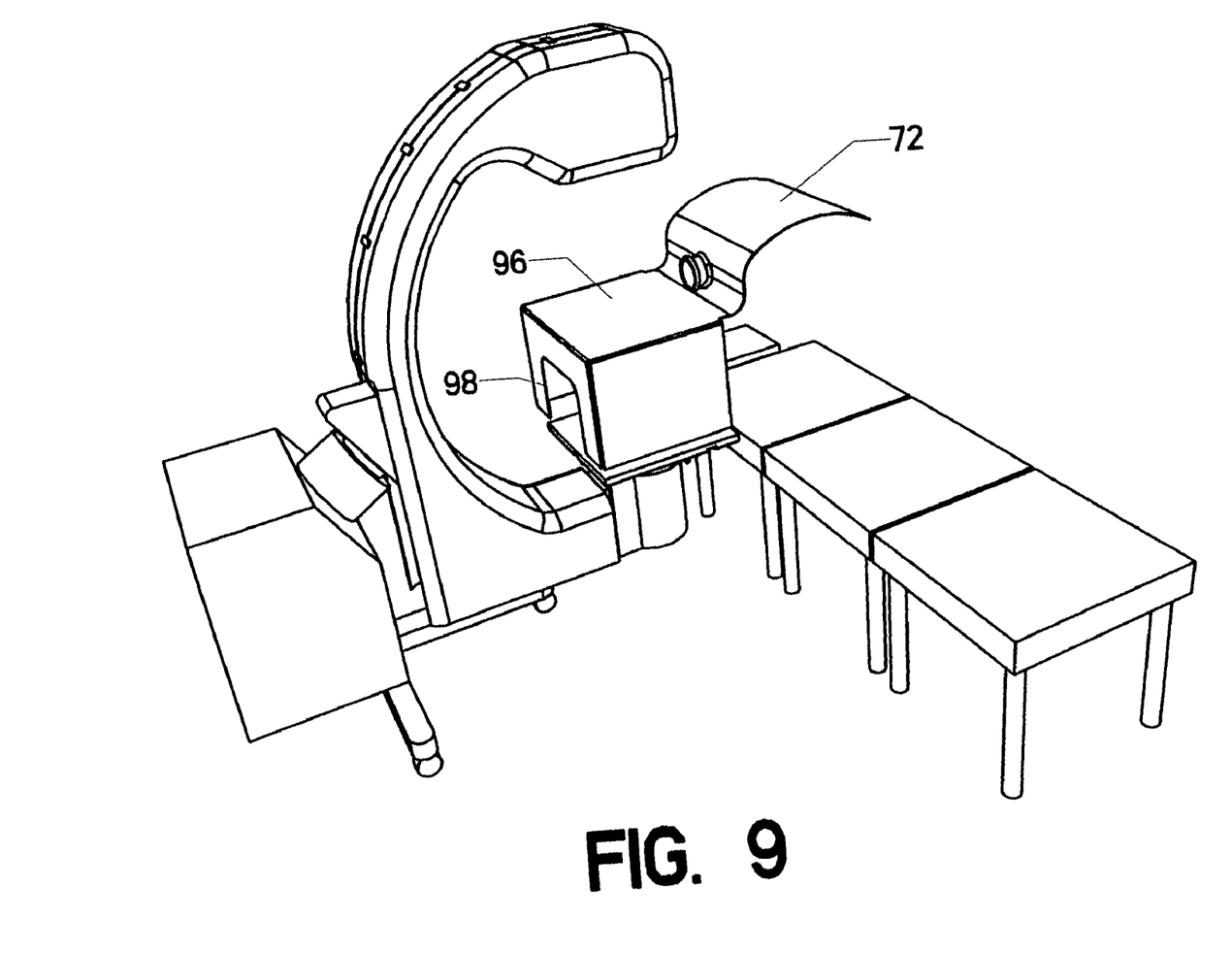
FIG. 9 is a perspective view, showing an alternate embodiment of the present invention.
Figure 10:
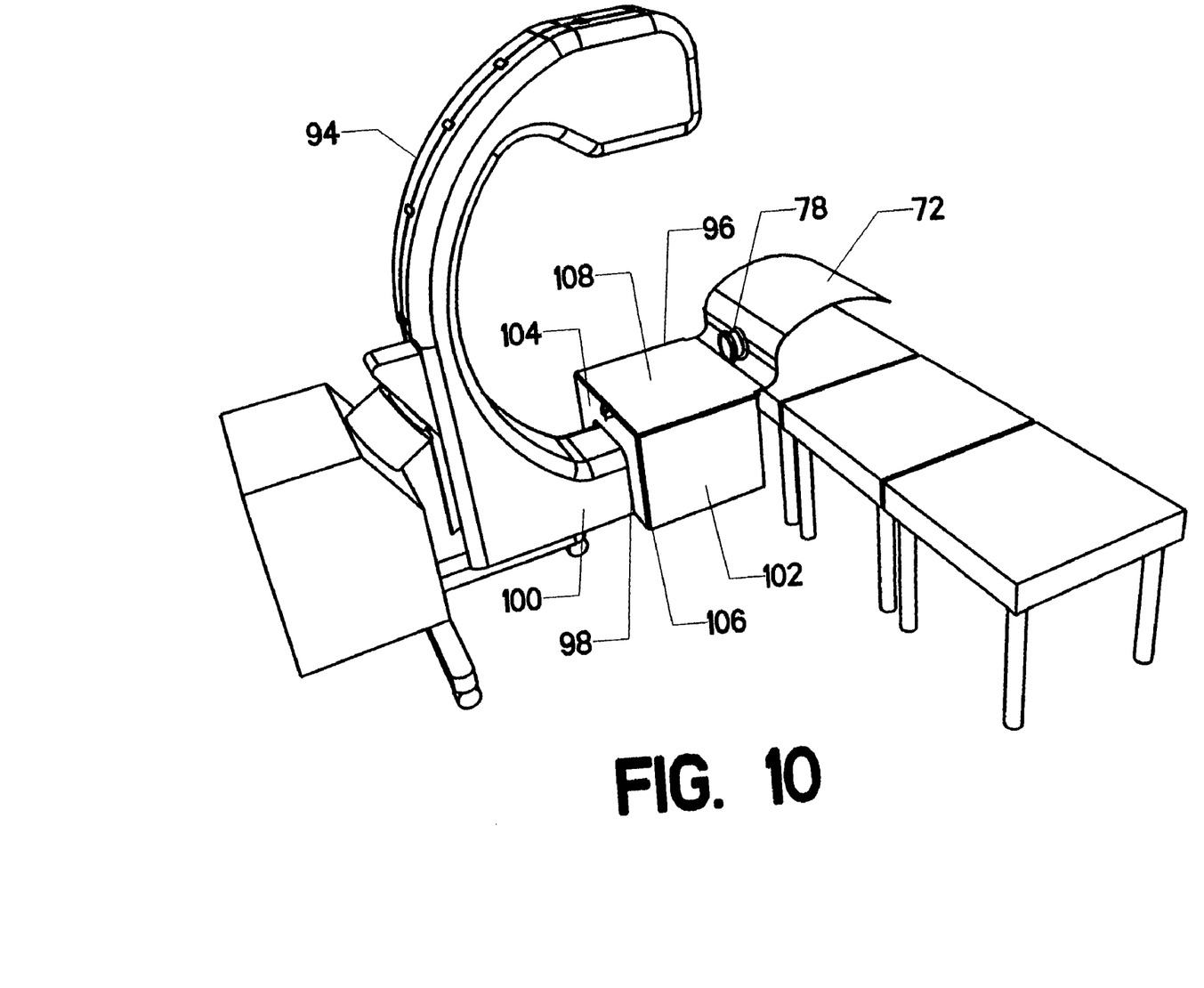
FIG. 10 is a perspective view, showing an alternate embodiment of the present invention.

In FIG. 9, table drape 96 is shown ready for installation, positioned over surgical table 32. Relief cut 98 is provided to allow it to slip over and around lower C-arm cover 100. FIG. 10 shows table drape 96 in the installed position. It may be desirable to join relief cut 98 to lower C-arm cover 100. This can be accomplished using VELCRO tabs or the like. Patient portion 72 is attached to table drape 96. It includes the same features (cuff 78, etc.) as are present for that portion of integrated drape 64. It can also be made separate from table drape 96, though it will likely need to be joined to the portion covering the table during installation.

Those skilled in the art will realize that the manufacturing of surgical drapes is analogous to pattern-making work involved in the manufacturing of clothing or furniture covers. Accordingly, it may be desirable to provide open seams in some areas that are closed during installation. Still referring to FIG. 10, the reader will observe that table drape 96 is composed generally of an upper panel 108 joined to two side panels 102 and an end panel 104 (the third side being open). Each side panel 102 is joined to end panel 104 along a seam 106. Table drape 96 could therefore be made as a flat pattern. It could then be folded into the shape shown during installation, with seams 106 being made by fasteners, such as adhesive tabs. Likewise, the complex shapes shown for C-arm drape 94 and integrated drape 64 could be devolved into a flat pattern that must be folded during installation. Such an approach is well known in the art and really makes no difference to the present invention.

Figure 11:
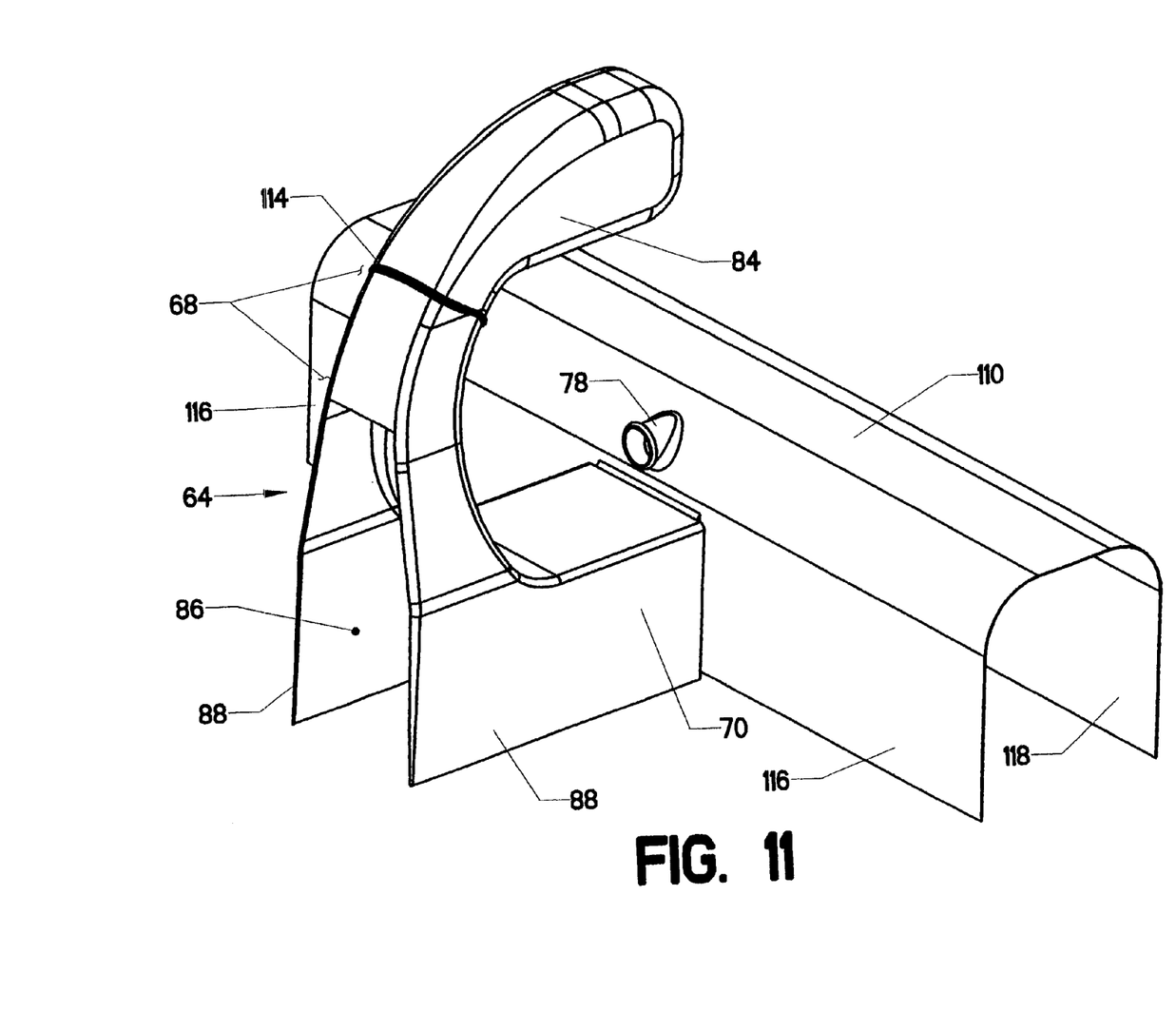
FIG. 11 is a perspective view, showing an alternate embodiment of the present invention.

It may be desirable to combine some of the previously described components into an integrated drape covering the entire patient. FIG. 11 shows such an embodiment. Integrated drape 64 contains one large portion for covering the C-arm and small surgical table, and a second large portion for covering the conventional table. Emitter enclosure 84 is a single tubular shape (omitting open seam 80). The tubular shape is large enough to slip over the emitter like a sock. Elastic strap 114 is placed on C-arm portion 68 to hold emitter enclosure 84 in place. An open seam 80, along with securing fasteners, could be used as well.

Two hanging portions 88 flank relief cut 86, which provides clearance for the supporting components of the C-arm machine. Table portion 70 is configured to cover surgical table 32. Integral table drape 110 is provided to cover conventional table 54. A cuff 78 is provided to allow the patient's arm to be exposed.

Figure 12:
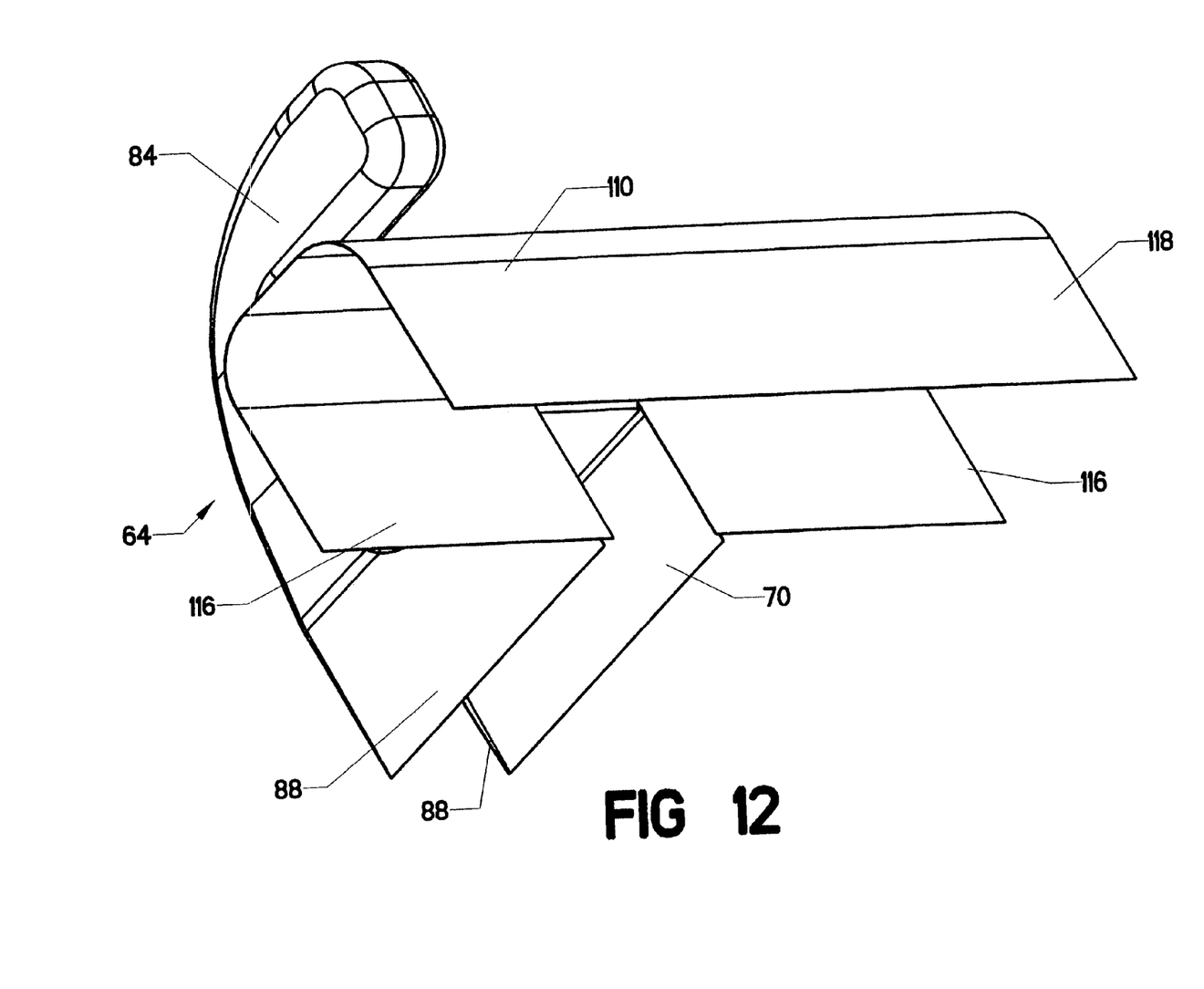
FIG. 12 is a perspective view, showing an alternate embodiment of the present invention.

FIG. 12 shows integrated drape 64 from the underside. Integrated table drape 110 has three descending flaps—denoted as two split flaps 116 and a single solid flap 118. The intersection between the two split flaps 116 and table portion 70 can be left open or sealed with adhesive flaps or other fasteners.

Those skilled in the art will realize that such a comprehensive drape should be ambidextrous. In other words, it should be capable of use in a surgery on a patient's left arm and right arm without substantial modifications. This fact dictates the symmetric nature of integral table drape 110.

Figure 13:
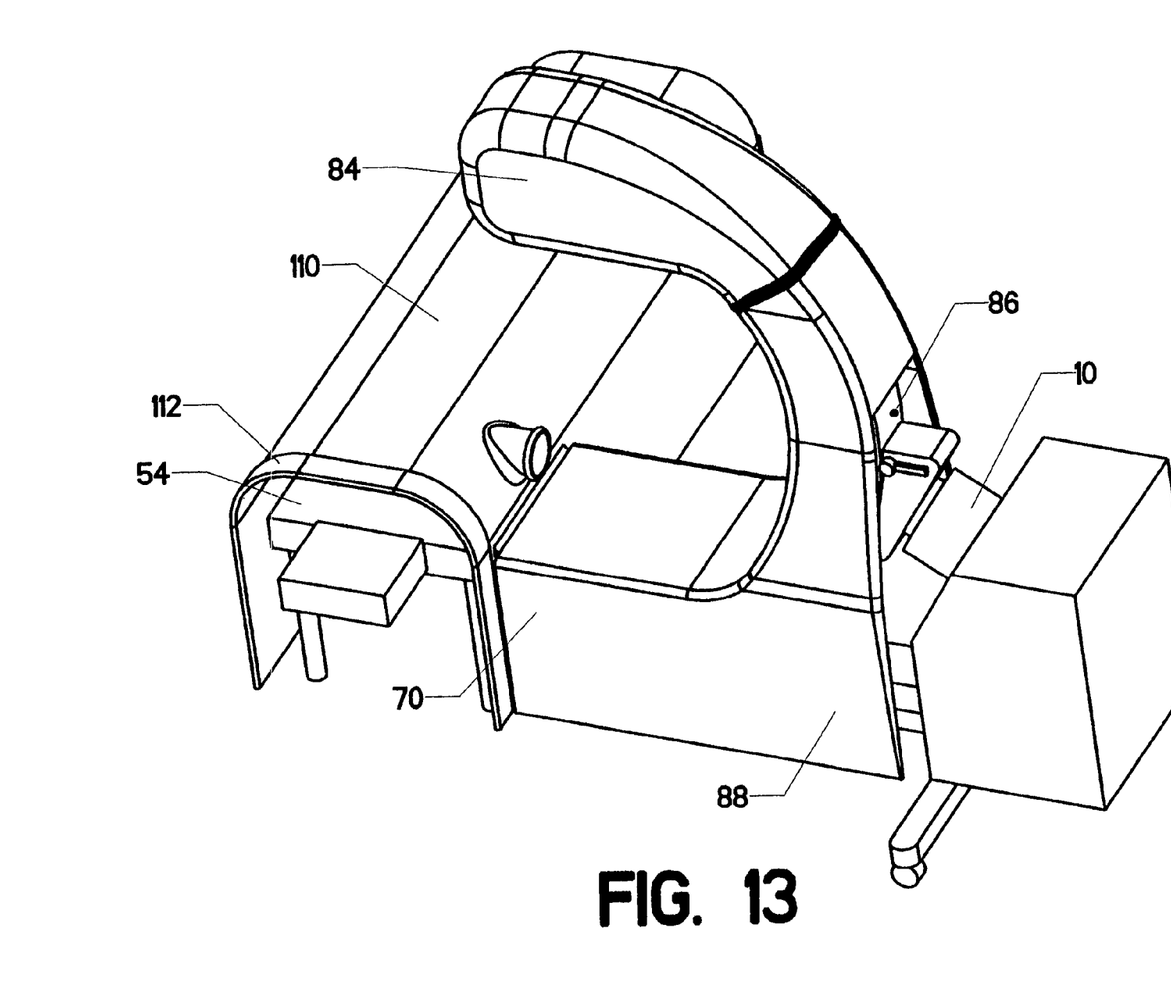
FIG. 13 is a perspective view, showing the application of the embodiment shown in FIG. 11 to a surgical table.
Figure 14:
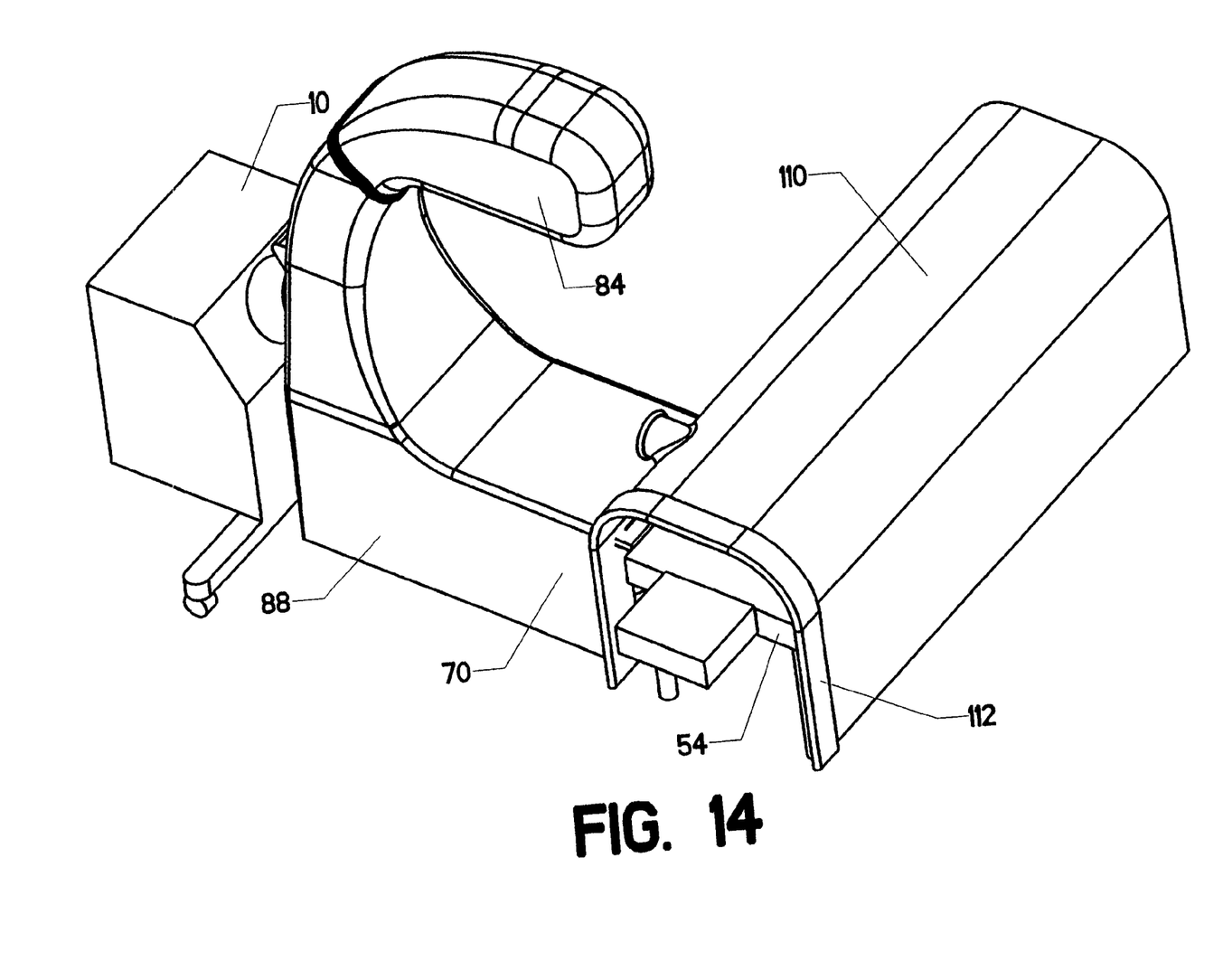
FIG. 14 is a perspective view, showing the application of the embodiment shown in FIG. 11 to a surgical table.

FIG. 13 shows the integrated drape in position for a surgery on a patient's right arm (assuming the patient is lying face up on conventional table 54). A substantial portion of integral table drape 110 has been rolled or folded to form fold back 112. FIG. 14 shows the integrated drape configured for a surgery on a patient's left arm. Again, the unneeded portion of table drape 110 has been rolled or folded to form fold back 112. It could also be cut free and removed. Surgical tape can likewise be employed to hold it in any desired position. Thus, the reader will appreciate that the embodiment shown in FIGS. 11–14 provides a unified drape which can be used to completely cover the desired portions of a patient. Such a drape can be made as a flat pattern. It can also be made by bonding together several separate subassemblies. It allows a surgeon to arrange the conventional table, small surgical table, and C-arm machine to his or her liking, then apply a single drape to provide the requisite sterile covering.

Figure 15:
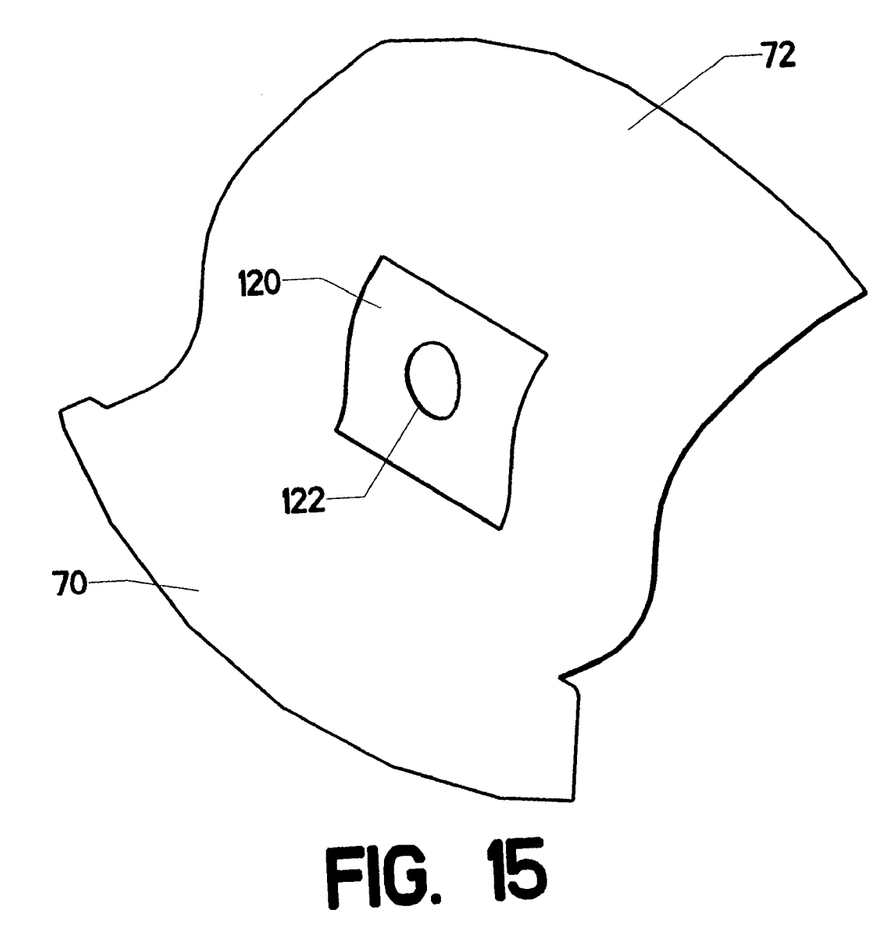
FIG. 15 is a perspective view, showing a different type of cuff

FIG. 15 shows an alternate type of cuff in common use. Flat panel cuff 20 is substituted for the sleeve-like cuff 78 shown previously. Flat panel cuff 20 is a sheet of elastic material bonded to the rest of the drape. Cuff hole 122 is positioned to allow the passage of the patient's arm therethrough. The elastic material expands to allow the passage of the patient's arm, while maintaining a seal around the arm. Although its structure is different from cuff 78, its function is the same. Those skilled in the art will know that many structures providing a seal around the patient's arm could be employed. For purposes of this disclosure, the term "cuff" is intended to cover all of these structures.

The preceding description contains significant detail regarding the novel aspects of the present invention. It is should not be construed, however, as limiting the scope of the invention but rather as providing illustrations of the preferred embodiments of the invention. As an example, the use of open seam 80 versus the tubular structure with securing strap 114 shown in FIGS. 11–14 should be viewed as interchangeable on all the embodiments. Thus, the scope of the invention should be fixed by the following claims, rather than by the examples given.

Having described my invention, I claim:

1. A sterile drape for covering a C-arm X-ray machine and a small surgical table attached thereto, wherein said C-arm X-ray machine has an emitter, a C-arm, an image intensifier, and C-arm mounting means, and wherein said small surgical table is attached to said image intensifier, comprising:
   a. a C-arm portion for covering said emitter and said C-arm;
   b. a table portion, for covering said small surgical table;
   c. wherein said C-arm portion opens into an open seam which, when opened, allows said C-arm portion to be slipped around and over said emitter and said C-arm; and
   d. closure means for closing said open seam when said sterile drape is in an installed position.

2. A sterile drape as recited in claim 1 and providing additional features for covering a patient, further comprising:
   a. a patient portion, attached to said table portion; and
   b. wherein said patient portion opens into a cuff, through which a portion of said patient may pass so as to lie over said table portion.

3. A sterile drape as recited in claim 2, wherein said cuff further comprises an elastic ring for gripping said portion of said patient passing therethrough.

4. A sterile drape as recited in claim 1, wherein said C-arm portion and said table portion are made as separate pieces which are joined together upon installation of said sterile drape.

5. A sterile drape as recited in claim 2, wherein said C-arm portion, said table portion, and said patient portion are made as separate pieces which are joined together upon installation of said sterile drape.

6. A sterile drape as recited in claim 1, wherein said C-arm portion opens into a relief cut positioned to allow clearance for said C-arm mounting means.

7. A sterile drape as recited in claim 1, wherein said sterile drape is made of X-ray transparent material.

8. A sterile drape as recited in claim 1, wherein the portions of said sterile drape lying over said emitter and said small surgical table are made of X-ray transparent material.

9. A sterile drape for covering a C-arm X-ray machine and a small surgical table attached thereto, wherein said C-arm X-ray machine has an emitter, a C-arm, an image intensifier, and C-arm mounting means, and wherein said small surgical table is attached to said emitter, comprising:
   a. a C-arm portion for covering said image intensifier and said C-arm;
   b. a table portion, for covering said small surgical table;

c. wherein said C-arm portion opens into an open seam which, when opened, allows said C-arm portion to be slipped around and over said image intensifier and said C-arm; and d. closure means for closing said open seam when said sterile drape is in an installed position.

10. A sterile drape as recited in claim 9 and providing additional features for covering a patient, further comprising:

c. a patient portion, attached to said table portion; and d. wherein said patient portion opens into a cuff, through which a portion of said patient may pass so as to lie over said table portion.

11. A sterile drape as recited in claim 10, wherein said cuff further comprises an elastic ring for gripping said portion of said patient passing therethrough.

12. A sterile drape as recited in claim 9, wherein said C-arm portion and said table portion are made as separate pieces which are joined together upon installation of said sterile drape.

13. A sterile drape as recited in claim 10, wherein said C-arm portion, said table portion, and said patient portion are made as separate pieces which are joined together upon installation of said sterile drape.

14. A sterile drape as recited in claim 9, wherein said C-arm portion opens into a relief cut positioned to allow clearance for said C-arm mounting means.

15. A sterile drape as recited in claim 9, wherein said sterile drape is made of X-ray transparent material.

16. A sterile drape as recited in claim 9, wherein the portions of said sterile drape lying over said emitter and said small surgical table are made of X-ray transparent material.

17. A sterile drape for covering a C-arm X-ray machine, a small surgical table attached thereto, and a patient lying on a conventional table proximate said small surgical table, wherein said C-arm X-ray machine has an emitter, a C-arm, an image intensifier, and C-arm mounting means, and wherein said small surgical table is attached to said image intensifier, comprising:

a. a C-arm portion for covering said emitter and said C-arm;

b. a table portion, for covering said small surgical table; and c. an integral table drape for covering said patient lying on said conventional table.

18. A sterile drape as recited in claim 17 wherein said integral table drape includes a cuff, through which a portion of said patient may pass so as to lie over said table portion.

19. A sterile drape as recited in claim 18, wherein said cuff further comprises an elastic ring for gripping said portion of said patient passing therethrough.

20. A sterile drape as recited in claim 17, wherein said C-arm portion opens into a relief cut positioned to allow clearance for said C-arm mounting means.

21. A sterile drape as recited in claim 17, wherein said sterile drape is made of X-ray transparent material.

22. A sterile drape as recited in claim 17, wherein the portions of said sterile drape lying over said emitter and said small surgical table are made of X-ray transparent material.

23. A sterile drape as recited in claim 17, wherein said integral table drape is symmetric and centered on said table portion, and wherein an unused portion of said integral table drape can be gathered into a fold back.

* * * * *